(12) United States Patent
Owens et al.

(10) Patent No.: US 7,104,755 B2
(45) Date of Patent: Sep. 12, 2006

(54) CEILING FAN WITH FRAGRANCE DISPENSING BLADE

(76) Inventors: Anthony Jerome Owens, 922 Linden Ave., Griffin, GA (US) 30223; Melissa Delphine Owens, 6735 Payne Ct., Cumming, GA (US) 30040

(*) Notice: Subject to any disclaimer, the term of this patent is extended or adjusted under 35 U.S.C. 154(b) by 0 days.

(21) Appl. No.: 11/366,955

(22) Filed: Mar. 2, 2006

(65) Prior Publication Data

US 2006/0177307 A1    Aug. 10, 2006

Related U.S. Application Data

(63) Continuation of application No. 10/858,813, filed on Feb. 9, 2005, now abandoned.

(51) Int. Cl.
*F04D 29/70* (2006.01)
(52) U.S. Cl. .................. 416/62; 416/146 R; 416/224
(58) Field of Classification Search .................. 416/62, 416/2, 224, 5, 146 R, 248, 210 R; D23/366, D23/368, 385
See application file for complete search history.

(56) References Cited

U.S. PATENT DOCUMENTS

| | | | |
|---|---|---|---|
| 4,753,573 A | 6/1988 | McKnight | |
| 4,840,650 A | 6/1989 | Matherne | |
| 4,889,543 A | 12/1989 | Burt | |
| 4,944,898 A | 7/1990 | Glaser | |
| 5,022,819 A | 6/1991 | Murcin et al. | |
| 5,082,422 A | 1/1992 | Wang | |
| 5,256,476 A | 10/1993 | Tanaka et al. | |
| 5,341,565 A | 8/1994 | Kuryliw | |
| 5,369,836 A | 12/1994 | Horne | |
| 5,383,765 A | 1/1995 | Baxter et al. | |
| 5,460,787 A | 10/1995 | Colon | |
| 5,562,412 A | 10/1996 | Antonelli | |
| 5,775,876 A | 7/1998 | Walker et al. | |
| 5,795,131 A | 8/1998 | Crowhurst et al. | |
| 5,935,526 A | 8/1999 | Moore | |
| 5,947,686 A | 9/1999 | Keyes | |
| 6,413,047 B1 | 7/2002 | Green | |
| 6,613,287 B1 | 9/2003 | McElligott | |
| 6,994,522 B1 * | 2/2006 | Chin-Chih et al. | 416/146 R |
| 2004/0247440 A1 | 12/2004 | Boubin | |

* cited by examiner

*Primary Examiner*—Richard A. Edgar
(74) *Attorney, Agent, or Firm*—John C. Gaydos

(57) ABSTRACT

A fan blade is provided with a recess for mounting an air freshener insert therein. The air freshener insert, after being mounted in the recess provided in the blade, releases a fragrance which is dispersed in the air when the fan blade is in rotary motion due to airflow over the air freshener insert.

3 Claims, 1 Drawing Sheet

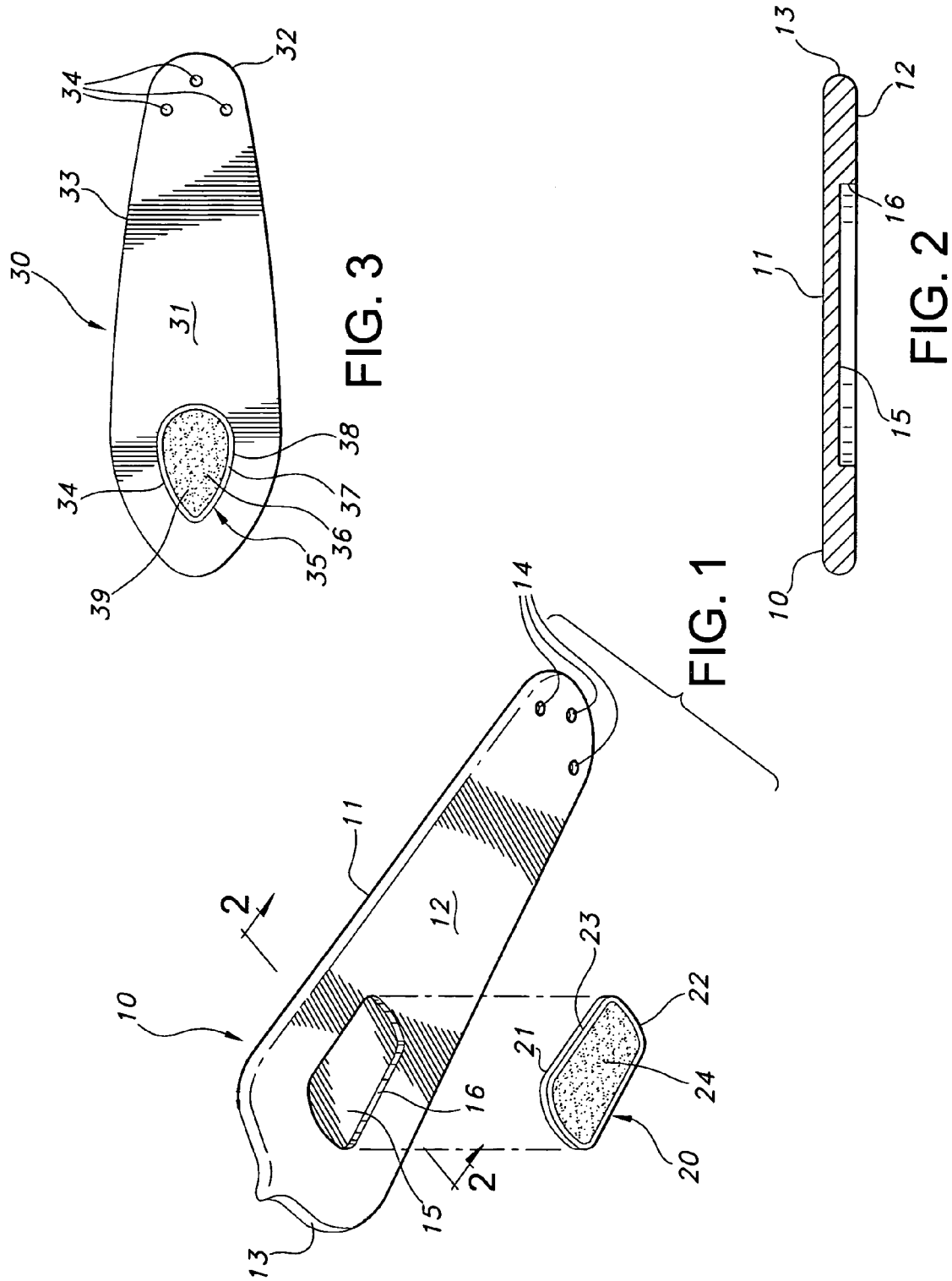

CEILING FAN WITH FRAGRANCE DISPENSING BLADE

CROSS REFERENCE TO RELATED APPLICATION

This application is a continuation of prior application Ser. No. 10/858,813, filed Feb. 9, 2005, now abandoned, and such specifically enumerated prior application is hereby incorporated by reference.

FIELD OF INVENTION

The present invention relates to a ceiling fan assembly for dispensing scent and, more particularly, to an improved ceiling fan assembly having a fan blade provided with a recess for receiving an air freshener insert.

BACKGROUND OF THE INVENTION

Rooms of a home can often take on strong odors. If a meal with strong-smelling food has recently been prepared in a kitchen, the cooking odors can often spread to different rooms of the home. Other odors from trash cans or toilets may also linger in bathrooms, bedrooms or kitchens.

In order to eliminate these odors, there are various steps that can be taken. Air freshener sprays can be sprayed around a room or a window can be opened to allow fresh air to enter a room. Other methods of eliminating odors include thoroughly cleaning a room or using a solid or plug-in air freshener.

A prior art ceiling fan blade assembly comprises a housing, an electric motor mounted in the housing, a plurality of fan blades secured to the shaft of the motor, and in a majority of fan blade assemblies on the market, a light bulb depends from the housing. Electric wires connect the motor and the light bulb to the home's electrical system. According to applicant's invention, the fan blade is provided with a recess and an air freshener insert is designed to snap into the recess and contains a scented oil, gel, or the like.

DESCRIPTION OF BACKGROUND ART

Boubin U.S. Pat. Appl. Pub. No. US2004/0247440, Keyes U.S. Pat. No. 5,947,686, and other prior art patents, attach an external air freshener dispenser to the outside or outer surface of a fan blade. Kuryliw U.S. Pat. No. 5,341,565, and other prior art patents, form a cavity or perforation through both surfaces of a fan blade for receiving a filter element that filters the air when the fan blade and filter are in rotary motion. However, the prior art does not suggest or teach that the filters receive, disperse, or dispense a solid, liquid or gaseous fragrance and the filters are not so designed. The blades and filters are incapable of dispersing or dispensing the fragrance as no reservoir is shown in the prior art patents. It would therefore be desirable to provide a fan blade with a built-in air freshener instead of attaching an external air freshener to the outside of the fan blade.

In view of the foregoing, it is an object of the present invention to provide an improved ceiling fan blade assembly with a built-in air freshener insert in the blade.

Another object of the present invention is to provide a ceiling fan blade assembly with an air freshener insert that is replaceable in a simple and facile manner.

A further object of the present invention is to provide a ceiling fan blade assembly capable of storing and dispensing a fragrance, e.g., a liquid or gel, from the air freshener insert.

Additional objects and advantages will become apparent to one skilled in the art and still other advantages will become apparent hereinafter.

BRIEF SUMMARY OF INVENTION

In summary, to accomplish the foregoing and other objects of the present invention, there is provided a ceiling fan blade assembly comprising a fan blade provided with a recess in the ceiling fan blade adapted to receive an air freshener insert. The insert, when fixedly attached to the ceiling fan blade, is located in the blade. The air freshener insert contains a fragrance bearing gel which disperses fragrance in the surrounding air when the ceiling fan blade is in rotary motion.

BRIEF DESCRIPTION OF THE DRAWINGS

For a further understanding of the objects of the present invention, reference should be had to the detailed description given hereinbelow with the accompanying drawings which are given by way of illustration only, and thus are not limitative of the present invention, and wherein:

FIG. 1 is a bottom perspective view of a preferred embodiment of a blade of a ceiling fan blade assembly (not shown) having a recess in the bottom surface of the blade and an air freshener insert adapted to be inserted into the recess;

FIG. 2 is a cross-sectional view along a line 2—2 of FIG. 1 further illustrating the recess located in the bottom surface of the blade; and FIG. 3 is a top view of another preferred embodiment of a blade of a ceiling fan blade assembly (not shown), the blade being provided with a recess, and an air freshener insert is mounted in the recess provided in the blade.

DETAILED DESCRIPTION OF THE INVENTION

In accord with the present invention, FIG. 1 illustrates a blade 10 of a ceiling fan assembly (not shown) having a top surface 11 and a bottom surface 12 defining a thickness 13. Bolts (not shown) are inserted into holes 14 provided in the inner portion of the blade 10 to secure the blade 10 to a hub (not shown) of the ceiling fan blade assembly preferably rotated by an electric pancake motor (not shown). The blade 10 according to the present invention is provided with a recess 15 in the bottom surface 12 of the blade 10. The recess 15 has a depth 16. An air freshener 20 being insertable into the recess 15, also hereinafter referred to an air freshener insert 20, is defined by a container 21 having a bottom wall 22 and side walls 23 for receiving a fragrance 24 containing a scent that is dispensed or dispersed into the air upon rotation of the blade 10 of a ceiling fan blade assembly.

It is to be understood that the fragrance 24 as used in the present invention refers to a solid, liquid, or gaseous carrier vehicle containing the scent. It is also to be understood that the thickness of the sidewalls 23 of the air freshener insert 20 can be greater or less than the thickness 13 of the blade 10 or the depth 16 of the recess 15 in the blade 10. Suitable means such as detents, resilient walls, and the like for fixedly securing the air freshener insert into the recess are well known in the art and will not be described in further detail herein.

In accord with the present invention, another preferred embodiment illustrates a blade 30 shown in FIG. 3 of the drawings having a top surface 31 and a bottom surface 32 defining a thickness 33. The blade 30 is provided with a recess 34 communicating with the top surface 31 for receiving an air freshener insert 35. The configuration of the recess 34 is not critical, the only requirement being that the air freshener insert 35 be provided with a mating configuration and with suitable means well known in the art for fixedly and detachably securing the insert 35 in the recess 34 to prevent accidental release of the insert 35 during operation of the ceiling fan assembly (not shown) and rotation of the blade 30. The air freshener insert 35 can be a plug of a solid fragrance dispensing material 36 that emits a scent or the fragrance material 36 can be deposited in a container 37 that is insertable into the recess 34. Preferably, and in accord with the present invention, the insert 35 provided with an outer surface 38 is flushably mounted with one of the surfaces 31 or 32 of the blade 30 and the same surface of the blade 30 is substantially flush with the surface 39 of the fragrance material 36. The insert 35 is provided with a periphery configured to the periphery of the recess 34. The air freshener insert 35 preferably is of the same density as the blade 30 to prevent the ceiling fan blade assembly (not shown) from vibrating unless the inserts 35 are inserted into opposing fan blades 30 secured to a hub (not shown).

To use the ceiling fan blade assembly, an owner installs the air freshener insert into the fan blade. When the fan blade assembly is in use, it creates a cool breeze, the light provides illumination and the breeze conveys the scent of the air freshener insert into a room or throughout the house. When the fan blade assembly is not in use, the air freshener insert continues to provide a pleasant scent in the room.

While two preferred embodiments have been described above, the present invention is not limited thereto, and it is to be understood that various changes in design can be made without departing from the scope of the claims.

The present invention being thus described, it will be obvious that the same can be varied in many ways. Such variations are not to be regarded as a departure from the spirit and scope of the invention, and all such modifications are to be included within the scope of the claims.

What is claimed is:

1. A ceiling fan assembly comprising:
at least one ceiling fan blade,
said at least one ceiling fan blade having a thickness defined between a top surface and a bottom surface,
wherein at least one of said surfaces has a recess provided therein,
wherein said recess has a depth smaller than said thickness such that said recess opens only to said surface having said recess provided therein and said recess is not in fluid communication with the other fan blade surface through said thickness;
and an air freshener,
wherein said air freshener is mounted in said recess.

2. The ceiling fan assembly of claim 1, wherein the recess is provided in the top surface of the blade.

3. The ceiling fan assembly of claim 1, wherein the recess is provided in the bottom surface of the blade.

* * * * *